(12) United States Patent
Purohit et al.

(10) Patent No.: US 12,213,680 B2
(45) Date of Patent: Feb. 4, 2025

(54) MEDICAL TREATMENT DEVICE AND RELATED METHODS THEREOF

(71) Applicant: Boston Scientific Medical Device Limited, Galway (IE)

(72) Inventors: Hitendra Purohit, Guj (IN); Agrim Mishra, Delhi (IN); Deepak Kumar Sharma, Muzaffarnagar (IN)

(73) Assignee: Boston Scientific Medical Device Limited, Galway (IE)

( * ) Notice: Subject to any disclaimer, the term of this patent is extended or adjusted under 35 U.S.C. 154(b) by 93 days.

(21) Appl. No.: 17/319,163

(22) Filed: May 13, 2021

(65) Prior Publication Data

US 2021/0353297 A1 Nov. 18, 2021

Related U.S. Application Data

(60) Provisional application No. 63/026,308, filed on May 18, 2020.

(51) Int. Cl.
*A61B 17/12* (2006.01)
*A61B 17/00* (2006.01)
*A61B 18/00* (2006.01)

(52) U.S. Cl.
CPC .... *A61B 17/1219* (2013.01); *A61B 17/12099* (2013.01); *A61B 17/12168* (2013.01);
(Continued)

(58) Field of Classification Search
CPC .......... A61B 17/1219; A61B 17/12099; A61B 17/12168; A61B 2017/00004; A61B 2017/00818; A61B 2017/00893; A61B 2017/12054; A61B 2018/00595; A61B 2217/005; A61B 18/1492; A61B 2018/00601; A61B 2090/3784;
(Continued)

(56) References Cited

U.S. PATENT DOCUMENTS 6,117,168 A * 9/2000 Yang ........................ A61L 31/16
623/1.44
9,913,655 B2 * 3/2018 Scheib .................... A61M 1/76
(Continued)

FOREIGN PATENT DOCUMENTS

DE 102008061536 A1 6/2010
DE 102014224012 A1 5/2016
WO 2017019810 A1 2/2017

OTHER PUBLICATIONS

International Search Report and Written Opinion issued Jul. 19, 2021 in International Application No. PCT/IB2021/054108 (12 pages).

*Primary Examiner* — Tan-Uyen T Ho
*Assistant Examiner* — David P Stein
(74) *Attorney, Agent, or Firm* — Bookoff McAndrews, PLLC

(57) ABSTRACT

A medical device, comprising a tube including at least one lumen, an absorbent located at a distal portion of the tube, the absorbent being configured to transition from a compressed state to an expanded state, and a structure fixed to the absorbent, wherein the structure is configured to flex into a compressed state and an expanded state simultaneously with the compressed state and the expanded state of the absorbent, and the structure exposes at least a portion of the absorbent.

20 Claims, 2 Drawing Sheets

(52) U.S. Cl.
CPC ............... *A61B 2017/00004* (2013.01); *A61B 2017/00818* (2013.01); *A61B 2017/00893* (2013.01); *A61B 2017/12054* (2013.01); *A61B 2018/00595* (2013.01); *A61B 2217/005* (2013.01)

(58) Field of Classification Search
CPC ...... A61B 2090/3966; A61B 17/12113; A61B 17/12159; A61B 17/12172; A61F 2220/0016; A61F 2230/0071; A61F 2/90; A61F 13/00068; A61F 2210/0061; A61M 1/916; A61M 2210/1042
See application file for complete search history.

(56) References Cited

U.S. PATENT DOCUMENTS

| | | | |
|---|---|---|---|
| 10,188,830 B2 * | 1/2019 | Loske | ................. A61M 25/005 |
| 2005/0240147 A1 * | 10/2005 | Makower | ............... A61B 10/06 |
| | | | 623/1.11 |
| 2009/0093809 A1 * | 4/2009 | Anderson | .......... A61B 18/1492 |
| | | | 606/41 |
| 2015/0306287 A1 * | 10/2015 | Burdick | ................. A61M 1/90 |
| | | | 604/319 |
| 2017/0312405 A1 | 11/2017 | Newton | |
| 2018/0228537 A1 * | 8/2018 | Dong | ........................ A61F 2/90 |
| 2019/0060609 A1 | 2/2019 | Loske | |
| 2020/0009303 A1 * | 1/2020 | Kleiner | ................. A61M 1/915 |
| 2020/0330660 A1 * | 10/2020 | Patel | ....................... A61M 1/77 |
| 2020/0360578 A1 * | 11/2020 | Loske | .................... A61F 13/36 |
| 2021/0268155 A1 * | 9/2021 | Burke | .................... A61M 1/85 |

\* cited by examiner

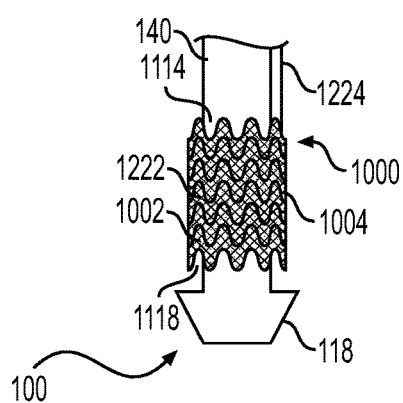
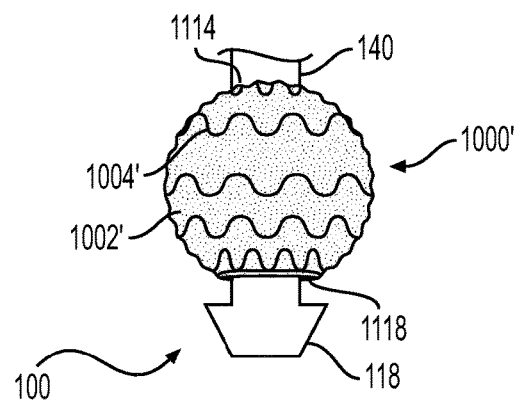
FIG. 1B
FIG. 1C
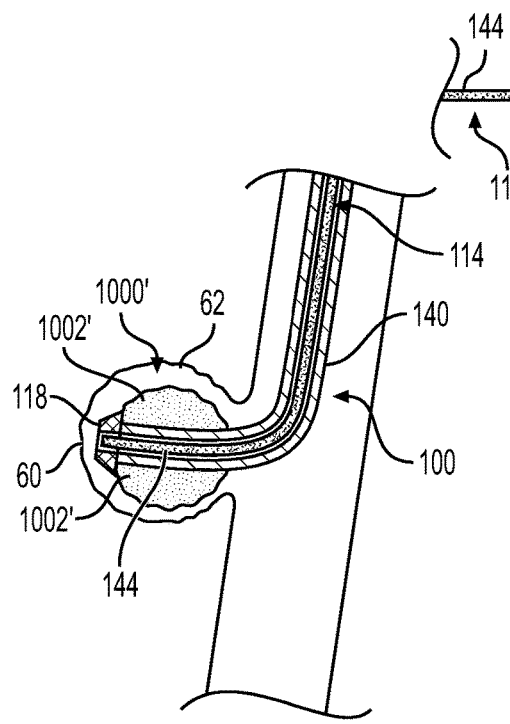
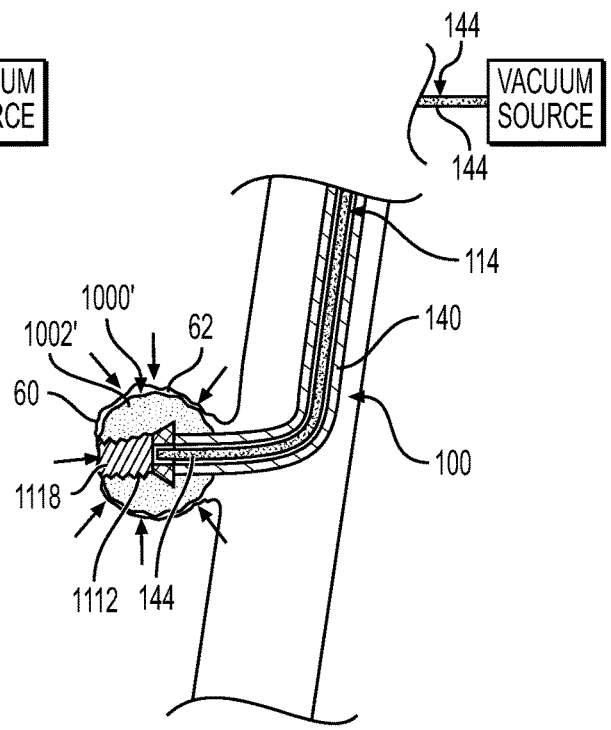
FIG. 2A
FIG. 2B

MEDICAL TREATMENT DEVICE AND RELATED METHODS THEREOF

CROSS-REFERENCE TO RELATED APPLICATIONS

This application claims the benefit of priority from U.S. Provisional Application No. 63/026,308, filed on May 18, 2020, which is incorporated by reference herein in its entirety.

TECHNICAL FIELD

Various aspects of the disclosure relate generally to medical treatment systems, devices, and related methods. Examples of the disclosure relate to medical treatment systems, and devices for treating wounds and defects along the gastrointestinal tract, among other aspects.

BACKGROUND

The gastrointestinal tract is a common anatomical site requiring medical attention and care. However, limited treatment options exist for managing gastrointestinal tract wounds or defects, such as esophageal perforations, ruptures, and also pancreatic cysts. Existing treatment options include surgical re-operation and endoscopic placement of a stent or clips. Surgery is relatively invasive and also has high morbidity and mortality rates. Endoscopic stent placement is a less invasive option. The placed stent, however, may require frequent surveillance.

SUMMARY

Aspects of the disclosure relate to, among other things, medical devices, and methods for treating a target treatment site, among other aspects. Each of the aspects disclosed herein may include one or more of the features described in connection with any of the other disclosed aspects.

According to an example, a medical device may comprise a tube including at least one lumen, an absorbent located at a distal portion of the tube, the absorbent being configured to transition from a compressed state to an expanded state, and a structure fixed to the absorbent, wherein the structure is configured to flex into a compressed state and an expanded state simultaneously with the compressed state and the expanded state of the absorbent, and the structure exposes at least a portion of the absorbent. The absorbent may comprise a foam, a sponge, a gel, or combinations thereof. The structure may include one or more woven wires. The structure may be fixed to the absorbent via adhesion, sewing, or molding. The absorbent may assume a substantially spherical configuration when in the expanded state.

According to another example, the medical device may further comprise a containment configured to maintain the absorbent in the compressed state. The containment may be a netting or a suture. The medical device may further comprise a wire coupled to a portion of the netting or suture, wherein the wire is configured to release the netting or suture from the absorbent by an application of a force to the wire, thereby transitioning the absorbent from the compressed state to the expanded state.

In another example, the absorbent may be exposed from within the structure. The at least one lumen may be configured to supply a vacuum to the distal end of the tube. The at least one lumen may include an actuation device, wherein the actuation device includes an inner lumen configured to supply a vacuum. The actuation device may be configured to extend distally and/or retract proximally within the at least one lumen. At least a portion of the structure may be coated with at least one drug. The medical device may further comprise an end effector, wherein the end effector is coupled to a distal portion of the tube. The end effector may comprise a cautery device.

According to an example, a medical device may comprise a tube including at least one lumen, an actuation device within the at least one lumen, wherein the actuation device is configured to move distally and proximally, and the actuation device is connectable with a vacuum, an absorbent at a distal portion of the tube, wherein the absorbent is configured to transition between compressed state and an expanded state, and a stent surrounding the absorbent, wherein the stent is fixed to an outer surface of the absorbent, and the stent exposes at least a portion of the absorbent. The stent may comprise a bioabsorbable material. The stent may comprise one or more woven wires, and wherein the wires include metal, plastic, or a combination thereof. The absorbent may include a cavity configured to contain a distal end of the tube when the tube is retracted into the cavity.

According to an example, a method of treating a subject may include introducing a medical device into a gastrointestinal system of the subject, positioning a distal portion of the medical device at a target site within the subject, the distal portion of the medical device including a stent containing an absorbent, wherein the stent and the absorbent are in a compressed state, expanding the stent and the absorbent of the medical device to occupy the target site of the subject, and supplying a vacuum to the target site through a lumen of the medical device.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 1B is a perspective view of a distal portion of the shaft of the medical device of FIG. 1A including an exemplary stent in a compressed configuration.

FIG. 1C is a perspective view of a distal portion of the shaft of the medical device of FIG. 1A including an exemplary stent in a deployed configuration.

FIGS. 2A-2B are cross-sectional views of the medical device of FIG. 1A illustrating an exemplary method of treating a wound, according to aspects of this disclosure.

DETAILED DESCRIPTION

Figure 1A:
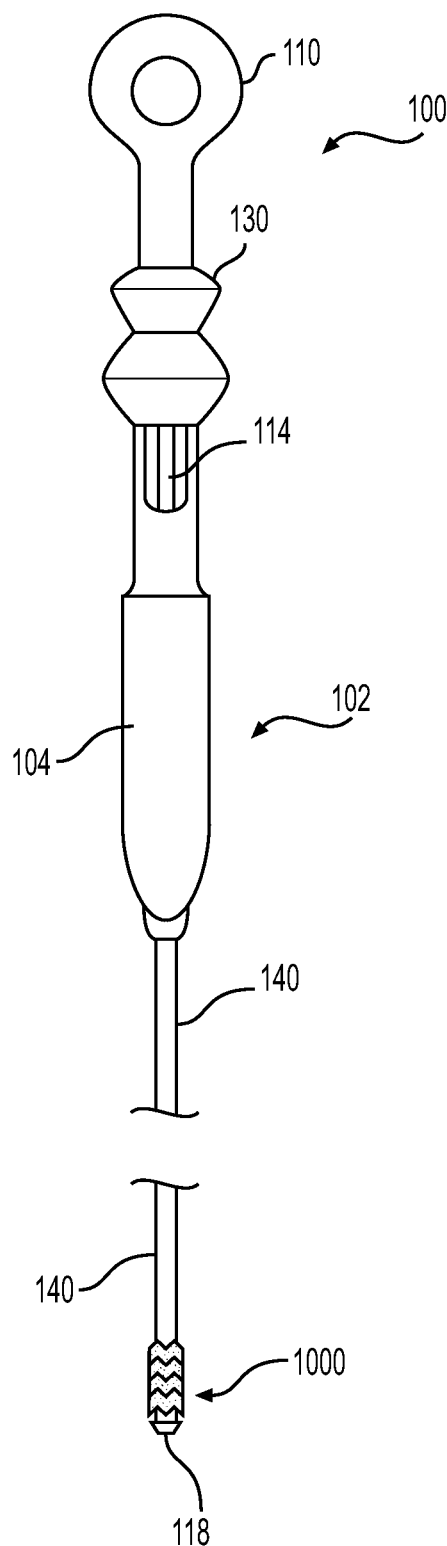
FIG. 1A is a perspective view of an exemplary medical device including a handle and a shaft, according to aspects of this disclosure.

Reference will now be made in detail to aspects of the disclosure, examples of which are illustrated in the accompanying drawings. Wherever possible, the same or similar reference numbers will be used throughout the drawings to refer to the same or like parts. The term "distal" refers to a location or portion of a medical device farthest away from a user of the device, e.g., when introducing a device into a subject (e.g., patient). By contrast, the term "proximal"

refers to a location or portion closest to the user, e.g., when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Embodiments of this disclosure include systems, devices, and methods for treating wounds and defects. Examples of said wounds and defects include those found along the gastrointestinal (GI) tract, such as perforations, tears, ruptures, leaks, anastomoses, and cysts, e.g., pancreatic cysts. Treatment of said wounds and defects may include placement of a stent, or any similar stent-like device, into the targeted site. Placement of the stent may be via a catheter, scope (endoscope, bronchoscope, colonoscope, etc.), tube, or sheath of a medical device, inserted into the GI tract via a natural orifice. The procedure may be performed with the assistance of suitable imaging modalities. For example, in one instance, the procedure may be an endoscopic ultrasound (EUS) procedure. The orifice can be, for example, the nose, mouth, or anus, and the placement can be in any portion of the GI tract, including the esophagus, stomach, duodenum, large intestine, or small intestine. Placement also can be in other organs reachable via the GI tract. After placement, negative pressure may be delivered to the targeted site via a lumen of a catheter of a medical device, which may be connected to a vacuum source.

In embodiments of this disclosure, the stent, or any similar stent-like device, may comprise a structure having a plurality of openings to an inner cavity of the stent, e.g., comprising a plurality of woven wires. The structure may comprise any suitable bioabsorbable material, e.g., bioabsorbable metal, plastic, etc., or combinations thereof, e.g., metal and plastic. The bioabsorbable material may be a flexible material, thereby allowing the stent to flex in response to a sufficient degree of force. For stents of a wire structure, the thickness of the wires is not particularly limited, so long as the wires are capable of flexing. The shape of the stent is not particularly limited as well, and may be spherical, cylindrical, etc. In some instances, the shape of the stent may be in accordance with the shape of the defect intended for treatment. The stent may also include at least two openings, e.g., a proximal and distal opening, configured to receive a catheter or scope, for delivering said stent. The at least two openings may be of any suitable size which allows for the stent to remain on said catheter during delivery thereof. The at least two openings may also be of a suitable size allowing the catheter to be retracted partially and/or removed completely from said stent. The stent may also include suitable indicia to assist with medical imaging, e.g., one or more radiopaque marker(s), which may be identifiable under various imaging techniques (e.g., x-ray). This may allow for easier surveillance and deployment of the stent.

Furthermore, in embodiments of this disclosure, the stent may include an absorbent body, e.g., a foam, sponge, gel, etc. The absorbent body may comprise any suitable bioabsorbable material, or combination of materials, that absorbs liquids. The absorbent body may also be of a suitable biocompatible flexible material. The absorbent body may be fixed to at least a portion of an inner and/or outer surface of the stent structure. Thus, at least a portion of the absorbent body may be exposed through the openings of the stent's structure. The manner in which the absorbent body is fixed to the stent is not particularly limited. The absorbent body may be adhered via a suitable adhesive, sewn, molded, etc. onto a surface of the stent, depending on the absorbent body. For example, a foam or sponge may be adhered via a suitable adhesive or sewn onto an inner surface of the stent. In another example, a gel, which may initially be in a tissue-paper like form, may be molded on to the inner surface of the stent structure. In some exemplary embodiments, the absorbent body may also be fixed to at least a portion of an outer surface of the stent structure. The absorbent body may be fixed to said outer surface in the same manner (or a different manner) as it is fixed to said inner surface of the stent. The outer surface of the stent may be additionally coated with any suitable coatings, e.g., one or more drug(s), including those which help with fluid absorption, reduce fluid generation, and/or tissue inflammation.

The thickness of the absorbent body is not particularly limited. In some examples, the absorbent body may be a lining on the inner surface (or outer surface) of the stent. In other examples, the absorbent body may be of such thickness so that it occupies a significant portion of the stent's cavity. In some other examples, a portion of the stent's cavity may remain open so that a catheter may extend through the proximal and distal openings of the stent.

Due to the flexible nature of the stent's structure and the absorbent body, the stent may include a compressed configuration and a deployed configuration. The aforementioned configurations are described in further detail below, when referring to FIGS. 1B and 1C. Furthermore, once deployed within a targeted site, the stent may further flex and take the shape of the targeted site, e.g., defect or cyst. This may help treat the targeted site by, for example, absorbing fluid in the targeted site, blocking further generation of fluid, and/or helping close open wounds.

Referring now to the figures, FIG. 1A shows an exemplary medical device 100 in accordance with an example of this disclosure. However, it is noted that device 100 is not limited to the below description, and that any suitable device, configured to deliver a stent, may be used. Medical device 100 may include a handle 102, an actuation wire 114, an actuator 130, and a shaft 140. Handle 102 may include a body 104 having a longitudinal length defined by a distal end and a proximal end. Handle 102 may define one or more lumens extending through body 104 between said distal and proximal ends. Handle 102 may further include a grasping feature 110 at its proximal end that is configured to be manually grasped by a user of medical device 100. In the example, grasping feature 110 may include a ring that is sized and/or shaped to receive a digit of a user therethrough (e.g., a thumb, etc.). In some other examples, grasping feature may be without a ring, and may include other grasping means.

Actuator 130 may be movably fixed onto a portion of handle 102 that is proximal to body 104 but distal the ring of grasping feature 110. Actuator 130 may be movable distally and proximally relative to handle 102. Handle 102 may be configured to receive actuation wire 114 through at least one lumen of body 104 (e.g., a working lumen). Actuation wire 114 may be fixed to actuator 130 such that movement of actuator 130 relative to handle 102 provides a simultaneous and corresponding movement of actuation wire 114 through a working lumen of body 104.

Actuation wire 114 has a longitudinal length defined between the proximal and distal ends (not shown) of wire 114. Actuation wire 114 may also include an inner lumen (not shown). Said inner lumen may be sized and shaped to receive one or more devices, or to serve as a delivery channel of fluid or negative pressure. For example, actuation wire 114 may include a proximal opening (not shown) at a proximal end that is configured to connect with one or more devices, such as a vacuum source. Thus, actuation wire 114 may be configured to supply negative pressure, through its inner lumen, to a distal opening (not shown) at the distal end of wire 114. However, it is noted that negative pressure is not limited to being supplied by actuation wire 114. In some other exemplary embodiments, negative pressure may be supplied via a lumen of shaft 140, or via another device extending through the lumen of shaft 140.

Still referring to FIG. 1A, shaft 140 may extend distally from body 104. Shaft 140 may define one or more lumens extending between a distal end and a proximal end of shaft 140. In some examples, at least one lumen of shaft 140 (e.g., a working lumen) may extend parallel to and be in coaxial alignment with at least one lumen of handle 102 (e.g., a working lumen) when shaft 140 is coupled to body 104. Accordingly, the working lumen of shaft 140 may receive actuation wire 114 therethrough from the working lumen of handle 102. A stent 1000 may also be fixed to a distal portion of shaft 140, as described in further detail below.

Medical device 100 may also include a cautery device 118 at the distal end of device 100. Cautery device 118 may be configured to cauterize (or otherwise cut) one or more materials (e.g., tissue) and/or objects positioned adjacent to the distal end of device 100, such as, for example, tissue. Cautery device 118 may be coupled to an electrical energy source (not shown) via one or more wires extending through corresponding lumens of handle 102 and shaft 140. However, it is noted that the distal end of device 100 is not limited to including cautery device 118, and may include any other suitable end effector.

FIG. 1B illustrates stent 1000, in a compressed configuration, fixed to a distal portion of shaft 140. Stent 1000 may be deliverable to a targeted site, e.g., a defect, cyst, etc., while in the compressed configuration. Stent 1000 includes a compressed absorbent body, e.g., foam 1002, and a compressed structure 1004, e.g., one or more woven wires, encapsulating (or encapsulated by) foam 1002. Stent 1000 may be formed to have any weave pattern, e.g., creating interstitial spacing as desired, and which may be filled and/or surrounded by foam 1002. As described above, foam 1002 may be fixed to the inner surface of structure 1004 via any suitable manner, e.g., adhesion. Stent 1000 further includes a proximal opening 1114 and a distal opening 1118. Openings 1114 and 1118 may be in fluid communication via a cavity of stent 1000 (not shown). Openings 1114 and 1118 may be shaped and sized to accommodate for shaft 140 extending through openings 1114 and 1118, and the cavity of the stent.

The manner by which stent 1000 is compressed is not particularly limited. For example, stent 1000 may be compressed via mechanical compression, vacuum compression, etc. To maintain stent 1000 in a compressed state, device 100 may further include a wrapping or netting 1222. Netting 1222 may be implemented to compress stent 1000 and to contain stent 1000, via the mechanical pressure of netting 1222. Netting 1222 may compress and contain stent 1000 so that device 100 may be deliverable through a working channel of a scope, e.g., an endoscope. Netting 1222 may be of any suitable materials and is not particularly limited. Suitable materials for netting 1222 include any suitable polymer, such as nylon or polypropylene. Other examples of mechanical compression may include keeping stent 1000 in a compressed state using a sheath or a wire mesh (not shown), or having stent 1000 with gel foam (not shown) and opening stent 1000 to decompress said foam. It is also noted that compression is not required in some other examples of stent 1000. For example, the absorbent body of stent 1000 may be of a gel form, which does not require compression. Such a gel absorbent may absorb liquid/fluid as the absorbent expands.

Device 100 may further include a control thread or a wire 1224 that is coupled to netting 1222. Wire 1224 may be coupled to a proximal portion of netting 1222, but is not limited thereto. Wire 1224 may be configured to shear or remove netting 1222 by a suitable force applied to wire 1224, e.g., a pulling force. Wire 1224 may extend through a lumen of shaft 140 or outside of shaft 140 (as shown), and a proximal end of wire 1224 may be connected to a controller or mechanism (not shown) configured to exert the necessary force to remove netting 1222. Alternatively, the proximal end of wire 1224 may be free and pulled proximally by the user. Thus, wire 1224 may assist in transitioning stent 1000 from a compressed configuration to a deployed configuration. In some other exemplary embodiments, netting 1222 may be formed of a material that will degrade or dissolve upon contact with fluid.

FIG. 1C illustrates stent 1000', in a deployed configuration, fixed to a distal portion of shaft 140. Stent 1000' may transition into a deployed configuration, from its compressed configuration, once delivered to a targeted site, e.g., a defect, cyst, etc. As shown, stent 1000' is generally spherical in shape. However, as noted above, the shape of stent 1000' is not particularly limited, and may be any suitable shape to fill a wound space. Foam 1002' may be in a default, expanded state, configured to take the shape of the targeted site, and to also absorb fluid from the targeted site. In some examples, foam 1002' may expand after removal of any mechanical constraint or containment, e.g., a netting or wrapping, of the foam. Structure 1004' may also expand as a result of the outward forces generated via the expansion of foam 1002'.

Referring to FIGS. 2A and 2B, an exemplary method of treating a defect or a cyst, via medical device 100, is further described. It is noted that prior to some procedures, preoperative imaging for procedure planning may take place. In an exemplary medical procedure, a user may introduce medical device 100 into a subject while stent 1000 (shown in FIGS. 1A and 1B) is in a compressed state. For example, a distal end of the medical device 100 may be introduced into the body of a subject via a natural orifice such as a mouth or anus. Medical device 100 may traverse through a tortuous natural body lumen of the subject, such as an esophagus, stomach, colon, etc. The distal end of the medical device 100 may be delivered via a scope, e.g., gastrointestinal scopes, EUS scope, or any other suitable way. In some examples, a guide wire (not shown) may be implemented to assist in the delivery of device 100. A user may direct/position the distal end of medical device 100 within a cavity 62 of a defect (or cyst) 60 of the subject, while stent 1000, which may be bioabsorbable, is still in a compressed configuration. In some examples, when treating a cyst, a user may use/activate cautery device 118 to tear an opening to cavity 62 of a cyst, prior to entering cavity 62. A user may then transition stent 1000 from its compressed configuration to stent 1000' in its deployed configuration, as shown in FIG. 2A. This transition may be effected by any suitable means, including removal of a mechanical constraint or containment (a netting), as described above.

As shown in FIG. 2A, stent 1000', once deployed and expanded into its spherical shape, may be anchored within cavity 62. While stent 1000' remains anchored, the distal end of device 100 may be retracted through a distal opening 1118 of stent 1000', so that the distal end of device 100 may remain within a cavity 1112 of stent 1000'. The manner by which the distal end of device 100 is retracted is not particularly limited, and in some examples, may be by a pulling force exerted by a user. As shown in FIG. 2B, actuation wire 114 may then be extended distally, via the distal movement of actuator 130 (shown in FIG. 1A), so that wire 114 is introduced within cavity 1112.

Still referring to FIG. 2B, negative pressure may be supplied through inner lumen 144 of actuation wire 114, by turning on a vacuum source connected to proximal end of wire 114. Said negative pressure may be supplied to cavity 1112 of stent 1000'. Furthermore, said negative pressure may be supplied to cavity 62 of defect (or cyst) 60, via opening 1118 and the porous channels of foam 1002'. By applying said negative pressure, fluid absorption via foam 1002' of stent 1000' may be expedited. Furthermore, said negative pressure, i.e., suction, may result in the walls of defect (or cyst) 60 contracting on to stent 1000'. This is illustrated by the directional arrows shown in FIG. 2B. This may assist in maximizing the amount of contact between defect (or cyst) 60 and an external surface of stent 1000'. Such contact may help with fluid absorption and blockage. Moreover, when treating cysts, such contact may help blocks pores on the cyst lining, which can reduce further fluid generation from cysts.

After delivering a sufficient amount of negative pressure to collapse defect (or cyst) 60 onto stent 1000', medical device 100 may be removed from stent 1000' altogether, while stent 1000' remains in cavity 62. It is noted that an additional, smaller stent may be deployed as the defect (or cyst) heals/closes over a duration of time.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

We claim:

1. A medical device, comprising:
   a first tube including at least one lumen;
   an absorbent located at a distal portion of the first tube, the absorbent being configured to transition from a compressed state to an expanded state, and wherein the first tube is movable relative to the absorbent;
   an actuation tube movable within the at least one lumen and relative to the absorbent, wherein a proximal opening of the actuation tube is connectable with a vacuum source, and a distal opening of the actuation tube is configured to supply a negative pressure;
   a structure fixed to the absorbent and including a cavity, wherein the cavity includes a distal opening and a proximal opening, wherein the structure is configured to flex into a compressed state and an expanded state simultaneously with the compressed state and the expanded state of the absorbent, and the structure exposes at least a portion of the absorbent; and
   a netting configured to maintain the absorbent in the compressed state,
   wherein the first tube extends through the distal opening and the proximal opening, thereby exposing a distal end of the first tube, and
   wherein only the actuation tube is configured to supply a negative pressure to the cavity and the absorbent when the distal end of the first tube and the distal opening of the actuation tube are within the cavity.

2. The medical device of claim 1, wherein the absorbent comprises a foam, a sponge, a gel, or combinations thereof.

3. The medical device of claim 1, wherein the structure includes one or more woven wires.

4. The medical device of claim 1, wherein the structure is fixed to the absorbent via adhesion, sewing, or molding.

5. The medical device of claim 1, wherein the absorbent assumes a substantially spherical configuration when in the expanded state.

6. The medical device of claim 1, further comprising a wire coupled to a portion of the netting, wherein the wire is configured to shear the netting from the absorbent by an application of a force to the wire, thereby transitioning the absorbent from the compressed state to the expanded state.

7. The medical device of claim 1, wherein the absorbent is exposed from within the structure.

8. A medical device, comprising:
   a first tube including at least one lumen;
   an absorbent located at a distal portion of the first tube, the absorbent being configured to transition from a compressed state to an expanded state, and wherein the first tube is movable relative to the absorbent;
   a structure fixed to the absorbent and including a cavity, wherein the structure is configured to flex into a compressed state and an expanded state simultaneously with the compressed state and the expanded state of the absorbent, and the structure exposes at least a portion of the absorbent;
   an actuation tube movable within the at least one lumen and relative to the absorbent, wherein the actuation tube is connectable with a vacuum source to supply a negative pressure to the absorbent via a distal opening of the actuation tube; and
   a wire coupled to a netting surrounding the absorbent and the structure, wherein
   the wire is configured to shear the netting to transition the absorbent from the compressed state to the expanded state,
   wherein a distal end of the first tube extends distally past the absorbent, thereby exposing the distal end of the first tube, and
   wherein the actuation tube is configured to supply the negative pressure to the absorbent when the distal end of the first tube and the distal opening of the actuation tube are within the cavity.

9. The medical device of claim 8, wherein the actuation tube is configured to extend distally and/or retract proximally within the at least one lumen.

10. The medical device of claim 1, wherein at least a portion of the structure is coated with at least one drug.

11. The medical device of claim 1, further comprising an end effector, wherein the end effector is coupled to the distal portion of the first tube.

12. The medical device of claim 11, wherein the end effector comprises a cautery device.

13. A medical device, comprising:
    a first tube including at least one lumen;

an absorbent at a distal portion of the first tube, wherein the absorbent is configured to transition between a compressed state and an expanded state;

an actuation device within the at least one lumen, wherein the actuation device is a second tube configured to move distally and proximally relative to the absorbent, and the actuation device is connectable with a vacuum source to supply a negative pressure to the absorbent;

a stent surrounding the absorbent, wherein the stent is fixed to an outer surface of the absorbent, and the stent exposes at least a portion of the absorbent; and a containment configured to maintain the absorbent in the compressed state, wherein the containment is a netting, a wrapping, or a suture, and wherein the stent includes a first opening and a second opening, wherein the first tube is configured to extend outside of the stent and the absorbent and retract within the stent and the absorbent through the first opening and the second opening, such that the first tube and the second tube are the only tubes within the stent and the absorbent.

14. The medical device of claim 13, wherein the stent comprises a bioabsorbable material.

15. The medical device of claim 14, wherein the stent comprises one or more woven wires.

16. The medical device of claim 13, wherein the absorbent further includes a cavity configured to contain a distal end of the first tube when the first tube is retracted into the cavity, and wherein the actuation device is configured to supply the negative pressure directly to the absorbent via a distal opening of the actuation device when the distal end of the first tube is retracted within the cavity of the absorbent.

17. The medical device of claim 12, wherein the cautery device is coupled to the exposed distal end of the first tube.

18. The medical device of claim 8, wherein the wire extends through a lumen of the first tube.

19. The medical device of claim 13, wherein the containment is a netting, and wherein the netting is coupled to a wire configured to shear the netting.

20. The medical device of claim 8, further comprising a cautery device coupled to the distal portion of the first tube.

* * * * *